United States Patent
Avolio et al.

(10) Patent No.: US 11,408,317 B2
(45) Date of Patent: Aug. 9, 2022

(54) METHOD AND DEVICE FOR DETERMINING THE EFFICIENCY OF AN SCR CATALYST

(71) Applicant: Vitesco Technologies GmbH, Hannover (DE)

(72) Inventors: Giovanni Avolio, Munich (DE); Sebastian Beer, Munich (DE); Mattia Perugini, Munich (DE)

(73) Assignee: VITESCO TECHNOLOGIES GMBH, Hannover (DE)

( * ) Notice: Subject to any disclaimer, the term of this patent is extended or adjusted under 35 U.S.C. 154(b) by 0 days.

(21) Appl. No.: 17/268,452

(22) PCT Filed: Aug. 5, 2019

(86) PCT No.: PCT/EP2019/070992
§ 371 (c)(1),
(2) Date: Feb. 13, 2021

(87) PCT Pub. No.: WO2020/043434
PCT Pub. Date: Mar. 5, 2020

(65) Prior Publication Data
US 2021/0180497 A1    Jun. 17, 2021

(30) Foreign Application Priority Data
Aug. 30, 2018   (DE) .................... 10 2018 214 788.4

(51) Int. Cl.
*F01N 3/20* (2006.01)
*F02M 26/06* (2016.01)
(Continued)

(52) U.S. Cl.
CPC .......... *F01N 3/208* (2013.01); *B01D 53/944* (2013.01); *B01D 53/9418* (2013.01);
(Continued)

(58) Field of Classification Search
CPC ........ F01N 3/208; F01N 3/2066; F01N 3/103; F01N 11/00; F01N 2550/02;
(Continued)

(56) References Cited

U.S. PATENT DOCUMENTS 8,347,611 B2 * 1/2013 Hepburn .................. F01N 9/00
60/297
8,833,059 B2 * 9/2014 Keppeler ............... F01N 3/2066
60/287
(Continued)

FOREIGN PATENT DOCUMENTS

CN      101787918 A    7/2010   ............ B01D 53/94
CN      102859152 A    1/2013   ............... F01N 3/20
(Continued)

OTHER PUBLICATIONS

Search Report for International Application No. PCT/EP2019/070992, 4 pages, dated Sep. 27, 2019.
(Continued)

*Primary Examiner* — Audrey B. Walter
*Assistant Examiner* — Dapinder Singh
(74) *Attorney, Agent, or Firm* — Slayden Grubert Beard PLLC

(57) ABSTRACT

Various embodiments include methods for determining the efficiency of an SCR catalytic converter in a system including a nitrogen oxide sensor, and a metering device for a reducing agent arranged in an exhaust-gas duct, and an exhaust recirculation line with a recirculation valve disposed downstream of the SCR catalytic converter and feeding an intake region of the engine. The methods comprise: setting or identifying a quasi-steady-state operating state and an associated recirculation rate; adding a first quantity of reducing agent using the metering device; measuring a resulting first nitrogen oxide value using the sensor; adding a further
(Continued)

predefined quantity, different from the first quantity; measuring the resulting nitrogen oxide values using the sensor; and determining the efficiency of the SCR catalytic converter based at least in part on the associated exhaust-gas recirculation rate and the measured nitrogen oxide values.

10 Claims, 3 Drawing Sheets

(51) Int. Cl.
    *F02M 26/14*      (2016.01)
    *B01D 53/94*      (2006.01)
    *F02D 41/00*      (2006.01)
    *F02M 26/17*      (2016.01)
    *G01N 33/00*      (2006.01)

(52) U.S. Cl.
    CPC ..... *B01D 53/9477* (2013.01); *B01D 53/9495* (2013.01); *F02D 41/0007* (2013.01); *F02D 41/0072* (2013.01); *F02M 26/06* (2016.02); *F02M 26/14* (2016.02); *F02M 26/17* (2016.02); *G01N 33/0037* (2013.01); *B01D 2255/904* (2013.01); *B01D 2255/91* (2013.01); *F01N 2610/146* (2013.01); *F01N 2900/1402* (2013.01); *F01N 2900/1411* (2013.01); *F02D 2041/0075* (2013.01)

(58) Field of Classification Search
CPC .......... F01N 2560/026; F01N 2610/00; F01N 2610/146; F01N 2900/1402; F01N 2900/1411; F01N 2900/0416; F01N 2900/1621; B01D 53/9418; B01D 53/944; B01D 53/9477; B01D 53/9495; B01D 2255/904; B01D 2255/91; F02D 41/0007; F02D 41/0072; F02D 41/1461; F02D 2041/0075; F02M 26/06; F02M 26/14; F02M 26/17; F02M 2026/001; G01N 33/0037; Y02T 10/12; Y02T 10/40

See application file for complete search history.

(56) References Cited

U.S. PATENT DOCUMENTS

| | | | |
|---|---|---|---|
| 10,053,103 B2 * | 8/2018 | Bevan | B60W 50/082 |
| 10,502,152 B2 * | 12/2019 | Kurtz | F01N 3/023 |
| 2009/0199537 A1 * | 8/2009 | Sisken | F01N 3/035 60/273 |
| 2010/0186390 A1 | 7/2010 | Perry et al. | 60/295 |
| 2013/0019588 A1 | 1/2013 | Richardson et al. | 60/274 |
| 2013/0269327 A1 | 10/2013 | Keppeler | 60/301 |
| 2013/0298533 A1 | 11/2013 | Kowalkowski et al. | 60/276 |
| 2015/0315951 A1 | 11/2015 | Veldten | F01N 11/00 |
| 2016/0144863 A1 | 5/2016 | Bevan et al. | 701/54 |
| 2016/0312719 A1 | 10/2016 | Veldten | F02D 41/00 |
| 2017/0122168 A1 | 5/2017 | Angst et al. | 60/274 |

FOREIGN PATENT DOCUMENTS

| | | | |
|---|---|---|---|
| CN | 103189633 A | 7/2013 | ............ F01N 3/20 |
| CN | 106640302 A | 5/2017 | ............ F01N 3/035 |
| DE | 102013007431 A1 | 10/2014 | ............ F01N 3/10 |
| DE | 10 2014 018037 | 6/2015 | ............ F01N 9/00 |
| DE | 10 2014 201000 | 7/2015 | ............ F01N 11/00 |
| EP | 1179667 A2 | 2/2002 | ............ F01N 3/08 |
| EP | 2 935 819 | 10/2016 | ............ F01N 3/08 |
| WO | 2017 098154 | 6/2017 | ............ F01N 3/20 |

OTHER PUBLICATIONS

Chinese Notice of Allowance, Application No. 201980056607.2, 9 pages, dated Jan. 6, 2022.

\* cited by examiner

METHOD AND DEVICE FOR DETERMINING THE EFFICIENCY OF AN SCR CATALYST

CROSS-REFERENCE TO RELATED APPLICATIONS

This application is a U.S. National Stage Application of International Application No. PCT/EP2019/070992 filed Aug. 5, 2019, which designates the United States of America, and claims priority to DE Application No. 10 2018 214 788.4 filed Aug. 30, 2018, the contents of which are hereby incorporated by reference in their entirety.

TECHNICAL FIELD

The present disclosure relates to internal combustion engines. Various embodiments may include methods and/or devices for determining the efficiency of an SCR catalytic converter of an exhaust-gas aftertreatment device of an internal combustion engine.

BACKGROUND

An exhaust-gas aftertreatment device in the exhaust-gas duct of an internal combustion engine, among other things, may reduce the content of nitrogen oxides in the exhaust gas of the internal combustion engine. This is achieved using so-called reduction catalytic converters, for example using SCR catalytic converters (SCR=Selective Catalytic Reduction). In these SCR catalytic converters, the nitrogen oxides contained in the exhaust gas are converted by means of a reducing agent added to the exhaust gas. This reducing agent is, for example, an aqueous urea solution, often also referred to as AdBlue.

In relation to the exhaust-gas mass flow, this urea solution is injected into the exhaust-gas duct upstream of the SCR catalytic converter in order to be able to convert the nitrogen oxides in the SCR catalytic converter. The exhaust-gas mass flow present downstream of the SCR catalytic converter then has a reduced nitrogen oxide content.

Some internal combustion engines have an exhaust-gas turbocharger. The structure, function and mode of operation of an exhaust-gas turbocharger have long been prior art. Furthermore, it is already known to supply a fraction of the exhaust-gas mass flow that is output from an SCR catalytic converter in the exhaust-gas duct of an internal combustion engine back to the intake region of the internal combustion engine via a low-pressure exhaust-gas recirculation system, possibly also via the compressor of the exhaust-gas turbocharger, and to admix said fraction to the fresh air that is also supplied.

Consequently, the compressed fresh air/exhaust gas mixture supplied to the internal combustion engine already contains a certain nitrogen oxide fraction, the concentration of which is dependent on the reducing action of the SCR catalytic converter. If the SCR catalytic converter causes a great reduction in the nitrogen oxides contained in the exhaust-gas mass flow of the internal combustion engine, then the nitrogen oxide fraction in the possibly compressed fresh air/exhaust gas mixture supplied to the internal combustion engine is low.

If, on the other hand, the SCR catalytic converter causes only a small reduction in the nitrogen oxides contained in the exhaust-gas mass flow of the internal combustion engine, then the nitrogen oxide fraction in the compressed fresh air/exhaust gas mixture supplied to the internal combustion engine is high. The more complete the reduction in the nitrogen oxides contained in the exhaust-gas mass flow of the internal combustion engine, the higher the efficiency of the SCR catalytic converter and thus of the exhaust-gas aftertreatment system as a whole.

The efficiency of an SCR catalytic converter is, apart from damage to the SCR catalytic converter, dependent primarily on the quantity of the reducing agent injected into the exhaust-gas duct into the exhaust-gas mass flow. In practice, there is therefore a need to meter the quantity of the reducing agent injected into the exhaust-gas duct as exactly as possible such that a high efficiency of the SCR catalytic converter is achieved. Precise knowledge of the present efficiency of the SCR catalytic converter makes it possible to meter the quantity of the reducing agent injected into the exhaust-gas duct such that the efficiency of the SCR catalytic converter is optimized.

The efficiency of an SCR catalytic converter can be ascertained for example using two nitrogen oxide sensors, of which one is arranged, in relation to the exhaust-gas mass flow, upstream of the SCR catalytic converter and the other is arranged downstream of the SCR catalytic converter in the exhaust-gas mass flow. A comparison of the output signals of these two nitrogen oxide sensors makes it possible to ascertain the efficiency of the SCR catalytic converter.

SUMMARY

The teachings of the present disclosure describe methods and devices for determining the efficiency of the SCR catalytic converter of an exhaust-gas aftertreatment device which, compared to the abovementioned prior art, exhibits a reduction in complexity and in particular a reduced number of parts or system components and can be carried out and implemented in a simple manner. For example, some embodiments include a method for determining the efficiency of an SCR catalytic converter (10) of an exhaust-gas aftertreatment device of an internal combustion engine (1), wherein the exhaust-gas aftertreatment device has an exhaust-gas duct (6) in which the SCR catalytic converter (10) is provided downstream of the internal combustion engine (1) with regard to the exhaust-gas mass flow, wherein a nitrogen oxide sensor (8) and a metering device (9) designed for adding a reducing agent are arranged in the exhaust-gas duct (6) between the internal combustion engine (1) and the SCR catalytic converter (10), and wherein a low-pressure exhaust-gas recirculation line (12) with an exhaust-gas recirculation valve (16) is provided between the exhaust-gas duct (6) downstream of the SCR catalytic converter (10) and an intake region (5) of the internal combustion engine (1), having the following steps: setting or identifying an at least quasi-steady-state operating state of the internal combustion engine (1) and an associated exhaust-gas recirculation rate in the low-pressure exhaust-gas recirculation line (12); adding a first predefined reducing agent quantity by means of the metering device (9) into the exhaust-gas duct (6) and measuring a resulting first nitrogen oxide value by means of the nitrogen oxide sensor (8), and subsequently; adding at least one further predefined reducing agent quantity, which differs from the previous reducing agent quantity, by means of the metering device (9) in the exhaust-gas duct (6) and measuring the resulting further nitrogen oxide values by means of the nitrogen oxide sensor (8), and determining the efficiency of the SCR catalytic converter (10) on the basis of the associated exhaust-gas recirculation rate and the measured nitrogen oxide values.

In some embodiments, an oxidation catalytic converter (7) is arranged in the exhaust-gas duct (6) between the internal combustion engine (1) and the metering device (9) for adding the reducing agent.

In some embodiments, in the course of the at least quasi-steady-state operating state, operating parameters of the internal combustion engine (1) are selected such that an exhaust-gas temperature that is elevated in relation to normal operation results therefrom, whereby the nitrogen oxide storage capacity of the SCR catalytic converter (10) is minimized.

In some embodiments, the first and/or the further added reducing agent quantity are each selected such that they are smaller than a maximum reducing agent quantity required for complete reduction of the nitrogen oxides in the exhaust-gas mass flow.

In some embodiments, the first and/or the further added reducing agent quantity are each selected such that the ratio $\alpha$ of the added reducing agent quantity to the maximum reducing agent quantity is less than or equal to 0.9 or less than or equal to 0.6 or less than or equal to 0.4.

In some embodiments, the ratio of the further added reducing agent quantity to the maximum reducing agent quantity differs from the ratio of the previously added reducing agent quantity to the maximum reducing agent quantity by an amount greater than or equal to 0.3 or greater than or equal to 0.2 or greater than or equal to 0.1.

As another example, some embodiments include a device for determining the efficiency of an SCR catalytic converter of an exhaust-gas aftertreatment device of an internal combustion engine, which device has an exhaust-gas duct (6) in which the SCR catalytic converter (10) is arranged downstream of the internal combustion engine (1) with regard to the exhaust-gas mass flow, wherein a nitrogen oxide sensor (8) and a metering device (9) designed for adding a reducing agent are arranged in the exhaust-gas duct between the internal combustion engine and the SCR catalytic converter (10), and wherein a low-pressure exhaust-gas recirculation line (12) with an exhaust-gas recirculation valve (16) is provided between the exhaust-gas duct downstream of the SCR catalytic converter (10) and an intake region of the internal combustion engine (1), characterized in that said device furthermore has an electronic control unit (13) which is designed for carrying out and controlling a method as claimed in any of the preceding claims.

In some embodiments, an oxidation catalytic converter (7) is arranged in the exhaust-gas duct (6) between the internal combustion engine (1) and the metering device (9) for adding the reducing agent.

In some embodiments, the electronic control unit (13) is connected to an electronic memory unit (14) in which data are stored which contain information and algorithms for determining the efficiency of the SCR catalytic converter (10).

In some embodiments, in the electronic memory unit (14), there are also stored data which contain information for setting or identifying an at least quasi-steady-state operating state of the internal combustion engine and/or for specifying the exhaust-gas recirculation rate in the low-pressure exhaust-gas recirculation line by means of the exhaust-gas recirculation valve and/or regarding the air mass flow to be supplied to the internal combustion engine and/or regarding the fuel mass flow to be supplied to the internal combustion engine.

BRIEF DESCRIPTION OF THE DRAWINGS

Further advantageous properties of various embodiments of the teachings herein will emerge from the exemplary explanation thereof, given with reference to the figures. In the figures.

Figure 1:
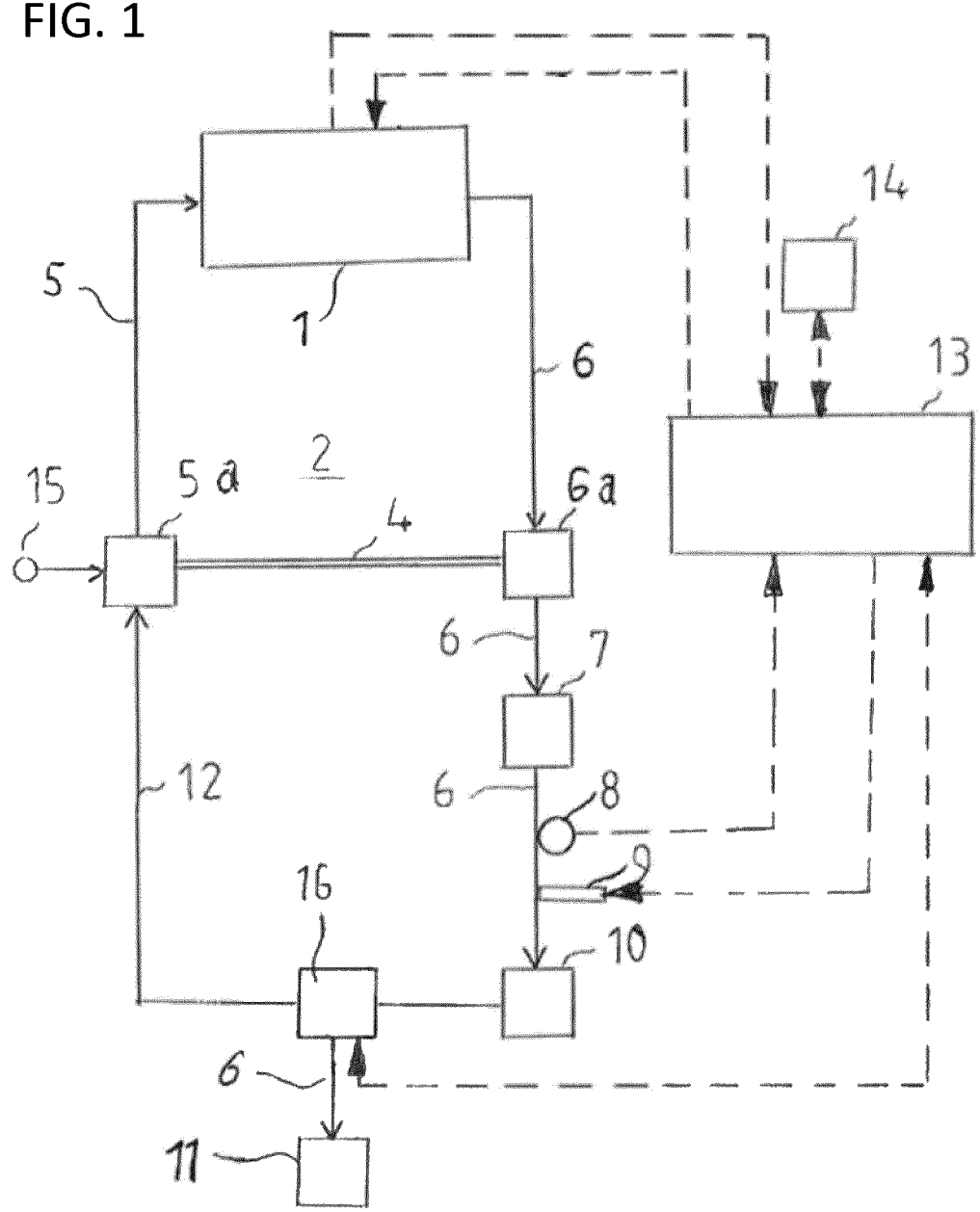
FIG. 1 is a block diagram showing an embodiment of a device incorporating teachings of the present disclosure for determining the efficiency of an SCR catalytic converter of an exhaust-gas aftertreatment device of an internal combustion engine.

In the figures, identical functional units are denoted throughout by the same reference designations.

DETAILED DESCRIPTION

The teachings of the present disclosure describe methods for determining the efficiency of an SCR catalytic converter of an exhaust-gas aftertreatment device of an internal combustion engine. In some embodiments, the exhaust-gas aftertreatment device has an exhaust-gas duct in which the SCR catalytic converter is provided downstream of the internal combustion engine with regard to the exhaust-gas mass flow, wherein a nitrogen oxide sensor and a metering device designed for adding a reducing agent are arranged in the exhaust-gas duct between the internal combustion engine and the SCR catalytic converter, and wherein a low-pressure exhaust-gas recirculation line with an exhaust-gas recirculation valve is provided between the exhaust-gas duct downstream of the SCR catalytic converter and an intake region of the internal combustion engine.

The method may include: setting or identifying an at least quasi-steady-state operating state of the internal combustion engine and an associated exhaust-gas recirculation rate in the low-pressure exhaust-gas recirculation line; adding a first predefined reducing agent quantity by means of the metering device into the exhaust-gas duct and measuring a resulting first nitrogen oxide value by means of the nitrogen oxide sensor, and subsequently; adding at least one further predefined reducing agent quantity, which differs from the previous reducing agent quantity, by means of the metering device in the exhaust-gas duct and measuring the resulting further nitrogen oxide values by means of the nitrogen oxide sensor, and determining the efficiency of the SCR catalytic converter on the basis of the associated exhaust-gas recirculation rate and the measured nitrogen oxide values.

In some embodiments, to implement the method with improved accuracy, while the method is being carried out, the internal combustion engine is operated in a steady-state or at least in an approximately steady-state operating state, which is referred to as quasi-steady-state operating state, in order to avoid disruptive influences owing to rapidly changing operating parameters. Here, the operating state or operating point of an internal combustion engine is determined significantly by rotational speed and load.

In a steady-state operating state, these parameters do not change, and in a quasi-steady-state operating state, these parameters change only slightly and in particular at such a low speed, that is to say with such shallow transients, that the effects on the implementation and the result of the method for determining the efficiency of the SCR catalytic converter are negligible. A change in the significant operating variables of less than or equal to 3% per 1 second (≤3%/1 S) can be assumed here for example as an acceptable value for the methods taught herein. In the context of this disclosure, an at least quasi-steady-state operating state is thus characterized in that the operating parameters of rotational speed and/or load of the internal combustion engine change no faster than 3%/1 S. To further increase the accuracy of the method, values less than 3%/1 S, in particular less than 2%/1 S or 1%/1 S, may also be specified.

In some embodiments, it is possible for two, three or more reducing agent quantities which differ from one another to be added, and the respective resulting nitrogen oxide concentrations detected, in chronological succession. To determine the efficiency of the SCR catalytic converter, in each case two of these values can then be compared. If multiple different reducing agent quantities are added, it is correspondingly possible for multiple pairs of detected nitrogen oxide concentrations to be formed and a respective efficiency determined. The accuracy of the methods can be increased by averaging the multiple efficiency values ascertained in this way.

In some embodiments, only a single nitrogen oxide sensor is required to determine the efficiency of an SCR catalytic converter. Said sensor is arranged upstream of the SCR catalytic converter and detects the nitrogen oxide concentration in the exhaust-gas mass flow output from the internal combustion engine. It is merely necessary, with the operating parameters of the internal combustion engine otherwise kept constant, to vary the added reducing agent quantity between at least two values in a chronological sequence and to detect the resulting nitrogen oxide concentration in each case. The knowledge of the at least two nitrogen oxide concentrations measured by means of this nitrogen oxide sensor in the exhaust-gas mass flow upstream of the SCR catalytic converter and the predefined exhaust-gas recirculation rate in the low-pressure exhaust-gas recirculation line make it possible for the efficiency of the SCR catalytic converter to be determined by means of a control unit which is generally present in any case.

In some embodiments, in the presence of an at least quasi-steady-state operating state with associated exhaust-gas recirculation rate, it is possible, by means of a variation in the quantity of the added reducing agent, for different resulting nitrogen oxide values to be measured by means of the nitrogen oxide sensor. As a consequence of adding the reducing agent, the nitrogen oxide content present in the exhaust-gas mass flow at the outlet of the SCR catalytic converter is reduced. Consequently, that part of the exhaust-gas mass flow which is recirculated via the low-pressure exhaust-gas recirculation line into the intake region of the internal combustion engine, and which is mixed with the supplied fresh air and optionally compressed and then supplied to the internal combustion engine, has a lower nitrogen oxide concentration. This in turn has the consequence that the exhaust-gas mass flow output from the internal combustion engine into the exhaust-gas duct has a reduced nitrogen oxide concentration. The nitrogen oxide concentration is measured by means of the nitrogen oxide sensor.

If, consequently, the exhaust-gas recirculation rate is known, the conversion rate and thus the efficiency of the SCR catalytic converter can be determined by varying the reducing agent quantity added to the exhaust-gas mass flow in the exhaust-gas duct.

In some embodiments, in the course of the quasi-steady-state operating state of the internal combustion engine, operating parameters of the internal combustion engine are selected, in particular controlled or adjusted to, for example by means of a central control unit assigned to the internal combustion engine, such that an exhaust-gas temperature that is elevated in relation to normal operation results therefrom, whereby the nitrogen oxide storage capacity of the SCR catalytic converter is minimized. Corresponding operating parameters may for example be the injection quantity in combination with the injection time of the fuel.

The above-described determination of the efficiency of the SCR catalytic converter may be carried out in the presence of comparatively high temperatures in the exhaust-gas duct as a whole, in order to circumvent the problem of the storage capacity of SCR catalytic converters. With increasing temperatures, the storage capacity of the SCR catalytic converter decreases and ultimately becomes negligibly small, such that the efficiency of the SCR catalytic converter can be determined with sufficient accuracy.

In some embodiments, the first and/or the further added reducing agent quantity are each selected such that they are smaller than a maximum reducing agent quantity required for complete reduction of the nitrogen oxides in the exhaust-gas mass flow. In the case of small, substoichiometric metering quantities of the reducing agent, it can be assumed with sufficient certainty that all of the reducing agent supplied to the exhaust-gas mass flow in the exhaust-gas pipe is involved in the conversion of the nitrogen oxides. Under these conditions, in the case of an intact, fully functional SCR catalytic converter, it can be assumed that the efficiency of the SCR catalytic converter corresponds with sufficient approximation to the ratio of added reducing agent quantity to the required maximum reducing agent quantity, which simplifies a mathematical determination of the actual efficiency. As the accuracy of adherence to this premise increases, so does the accuracy of the determination of the efficiency of the SCR catalytic converter.

In some embodiments, the first and/or the further added reducing agent quantity are each selected such that the ratio $\alpha$ of the added reducing agent quantity to the maximum reducing agent quantity is less than or equal to 0.9 or less than or equal to 0.6 or less than or equal to 0.4. In particular proceeding from a ratio of $\alpha=0.6$ and below, particularly accurate adherence to the abovementioned premise and thus a particularly accurate determination of the efficiency of the SCR catalytic converter can be expected. In particular, in the selection of the ratio $\alpha$, it is important that this is small enough to allow any possible inhomogeneities in the reducing agent preparation or the reducing agent infeed during operation to be disregarded.

Likewise, a further simplification of the mathematical determination of the efficiency of the SCR catalytic converter is achieved if the method according to the invention is carried out such that the respectively subsequent, further added reducing agent quantity is greater than the previously added reducing agent quantity. To further increase the reliability and the accuracy of the methods described herein, it may be advantageous if the ratio $\alpha$ of the further added reducing agent quantity to the maximum reducing agent quantity differs from the ratio $\alpha$ of the previously added reducing agent quantity to the maximum reducing agent quantity by an amount greater than or equal to 0.3 or greater than or equal to 0.2 or greater than or equal to 0.1. For example, the initially added reducing agent quantity thus may have a ratio of $\alpha=0.6$ or $\alpha=0.4$ and the subsequently added reducing agent quantity may have a ratio of $\alpha=0.9$ or $\alpha=0.6$. In the first case, the ratios differ by an amount of 0.3, in the second case by 0.2.

In some embodiments, a device incorporating teachings of the present disclosure for determining the efficiency of an SCR catalytic converter of an exhaust-gas aftertreatment device of an internal combustion engine has an exhaust-gas duct in which the SCR catalytic converter is arranged downstream of the internal combustion engine with regard to the exhaust-gas mass flow. Here, a nitrogen oxide sensor and a metering device designed for adding a reducing agent are arranged in the exhaust-gas duct between the internal combustion engine and the SCR catalytic converter, wherein a low-pressure exhaust-gas recirculation line with an exhaust-gas recirculation valve are provided between the exhaust-gas duct downstream of the SCR catalytic converter and an intake region of the internal combustion engine. The device according to the invention is furthermore characterized in that it furthermore has an electronic control unit which is configured to control and carry out a method according to the invention as described in the method claims.

In some embodiments, an oxidation catalytic converter is arranged in the exhaust-gas duct between the internal combustion engine and the metering device for adding the reducing agent. Here, the nitrogen oxide sensor may be arranged both upstream and downstream of the oxidation catalytic converter; only the arrangement upstream of the SCR catalytic converter is important here. The exhaust-gas aftertreatment device is thus supplemented by an additional component for removing carbon monoxide and residues of unburned hydrocarbon contained in the exhaust gas by oxidation with the residual oxygen in the exhaust gas, which is present in excess in the exhaust gas in particular in the case of lean combustion that is typical of diesel engines. This contributes significantly to an overall reduction of the constituents in the exhaust gas that are harmful to the environment and to health.

In some embodiments, the electronic control unit is connected to an electronic memory unit in which data are stored which contain information and algorithms for determining the efficiency of the SCR catalytic converter. In some embodiments, in the electronic memory unit, there are also stored data which contain information: for setting or identifying an at least quasi-steady-state operating state of the internal combustion engine and/or for specifying the exhaust-gas recirculation rate in the low-pressure exhaust-gas recirculation line by means of the exhaust-gas recirculation valve and/or regarding the air mass flow to be supplied to the internal combustion engine and/or regarding the fuel mass flow to be supplied to the internal combustion engine.

The connection of the control unit to an electronic memory unit and the storage of the abovementioned data allows the simple and permanent provision of certain specification values for the automatic, repeated implementation of the methods described herein.

The efficiency of the SCR catalytic converter can be determined both in conjunction with an optimization of the metering of the reducing agent injected into the exhaust-gas duct and for other purposes. Furthermore, catalytic converter aging, which affects the nitrogen oxide conversion rate, can also be derived from the determined efficiency.

The device illustrated in FIG. 1 has an internal combustion engine 1, in this case equipped with an exhaust-gas turbocharger 2 which comprises a turbine 6a having a turbine wheel, a rotor shaft 4 and a compressor 5a with a compressor wheel, and said device has an exhaust-gas duct 6, an electronic control unit 13, an electronic memory unit 14 and a fresh-air inlet 15. The turbine 6a with the turbine wheel, an oxidation catalytic converter 7, an SCR catalytic converter 10 and an exhaust-gas tailpipe 11 are arranged in the exhaust-gas duct 6.

From the exhaust-gas duct 6, downstream of the SCR catalytic converter 10 in the exhaust-gas mass flow, a low-pressure exhaust-gas recirculation line 12 leads to the compressor 5a belonging to the intake region 5 of the internal combustion engine. The low-pressure exhaust-gas recirculation line 12 has an exhaust-gas recirculation valve 16 for setting the exhaust-gas recirculation rate, said valve being arranged here directly in the branch of the low-pressure exhaust-gas recirculation line 12 from the exhaust-gas duct 6.

A nitrogen oxide sensor 8 and a metering device 9 are arranged in the exhaust-gas duct 6 between the oxidation catalytic converter 7 and the SCR catalytic converter 10, that is to say upstream of the SCR catalytic converter 10. By means of the nitrogen oxide sensor 8, the nitrogen oxide concentration ($c_{NOx,BKM}$) in the exhaust-gas mass flow ($m_{Exh,BKM}$) upstream of the SCR catalytic converter 10 (SCR-Kat) is measured. The measured values detected by the nitrogen oxide sensor 8 are supplied to and evaluated by the electronic control unit 13. A reducing agent, which is for example an aqueous urea solution, is added to the exhaust-gas mass flow in the exhaust-gas duct 6 by means of the metering device 9, which is actuated by the electronic control unit 13. This reducing agent mass flow ($m_{Rdm}$) supplied to the exhaust-gas duct is metered by the electronic control unit 13 by specification of a control signal to the metering device 9.

The partial exhaust-gas mass flow recirculated via the low-pressure exhaust-gas recirculation line 12 to the intake region 5 of the internal combustion engine 1, in this case into the compressor 5a, is mixed and compressed in the compressor 5a with the fresh air supplied to the compressor via the fresh-air inlet 15. The compressed fresh air/exhaust gas mixture is supplied to the internal combustion engine 1 via the intake region 5 and is supplied there to a combustion process together with an injected fuel quantity.

The exhaust gas formed in the process, which in turn has a nitrogen oxide concentration, is fed via the exhaust-gas duct 6 to the turbine 6a of the exhaust-gas turbocharger 2 and subsequently to the exhaust-gas aftertreatment device.

In some embodiments, both the exhaust-gas turbocharger 2 and the oxidation catalytic converter 7 do not necessarily need to be present, but these may be used in addition in a configuration level or an embodiment of the device.

The control unit 13 is designed and configured to carry out at least one of the methods described herein. For this purpose, it is connected, at least via corresponding signal lines illustrated by dashed lines in FIG. 1, to corresponding functional units of the internal combustion engine 1, the exhaust-gas recirculation valve 16, the metering device 9 and the nitrogen oxide sensor 8.

Figure 2:
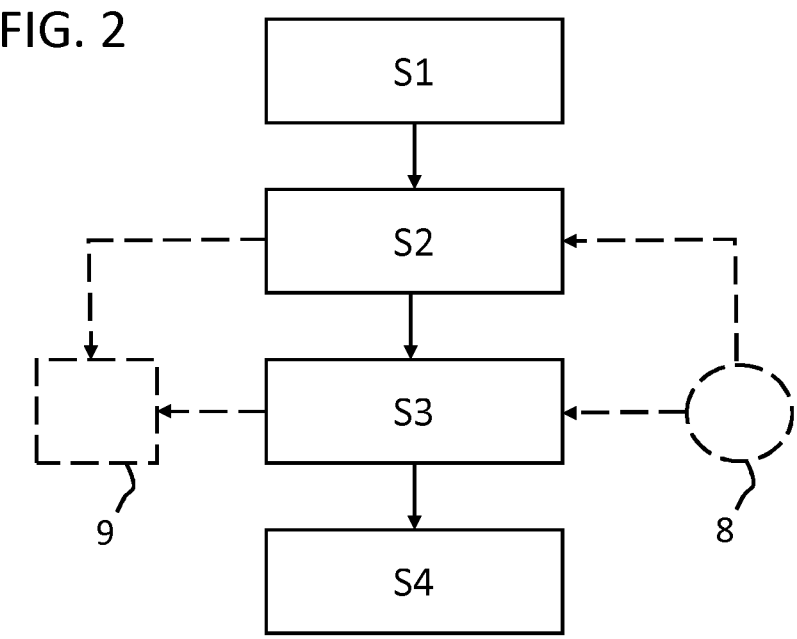
FIG. 2 is a simplified flow diagram for illustrating method steps of an embodiments of the teachings of the present disclosure.

The progression of the method then takes place for example as illustrated in FIG. 2. In a step S1, a steady-state operating state of the internal combustion engine 1 and an associated exhaust-gas recirculation rate are firstly set or identified. The exhaust-gas recirculation rate in the low-pressure exhaust-gas recirculation line 12 is set or adjusted to by means of the exhaust-gas recirculation valve 16; for this purpose, the electronic control unit 13 is connected, for example via corresponding signal lines illustrated by dashed lines in FIG. 1, to the respective functional units of the internal combustion engine.

In a step S2, a first predefined reducing agent quantity is added to the exhaust-gas duct 6 by means of the metering device 9 and a resulting first nitrogen oxide value is measured by means of the nitrogen oxide sensor 8. For this purpose, the electronic control unit 13 is connected to the metering device 9 and to the nitrogen oxide sensor 8 via signal connections, as can be seen from FIGS. 1 and 2.

In the subsequent step S3, at least one further predefined reducing agent quantity, which differs from the previous reducing agent quantity, is added to the exhaust-gas mass flow in the exhaust-gas duct 6 by means of the metering device 9, and the resulting further nitrogen oxide values are measured by means of the nitrogen oxide sensor 8.

Finally, in step S4, the efficiency of the SCR catalytic converter 10 is then determined on the basis of the associated exhaust-gas recirculation rate and the measured nitrogen oxide values.

In this determination of the efficiency of the SCR catalytic converter 10 (SCR-Kat), use is made of the fact that the exhaust-gas mass flow output from the internal combustion engine to the exhaust-gas duct 6 after a combustion process of the internal combustion engine 1 (BKM) has a nitrogen oxide concentration that correlates with the exhaust-gas recirculation rate of the partial exhaust-gas mass flow recirculated via the low-pressure exhaust-gas recirculation line 12 into the intake region 5 of the internal combustion engine 1.

The electronic control unit 13 can therefore determine the efficiency of the SCR catalytic converter (10) from a predefined exhaust-gas recirculation rate in the low-pressure exhaust-gas recirculation line 12 and from at least two values, measured by means of the nitrogen oxide sensor 8 in the case of the addition of different reducing agent quantities ($m_{Rdm}$), for the nitrogen oxide concentration upstream of the SCR catalytic converter 10.

To determine this efficiency, it is not necessary to use a further nitrogen oxide sensor arranged downstream of the SCR catalytic converter 10 to detect and evaluate the nitrogen oxide concentration present downstream of the SCR catalytic converter 10. The calculation algorithms required to ascertain the efficiency of the SCR catalytic converter 10, and other data required for this purpose, are stored for example in the electronic memory 14 and are created or empirically ascertained by the manufacturer in advance. The electronic control unit 13 can access these data when determining the efficiency of the SCR catalytic converter 10.

Figure 3:
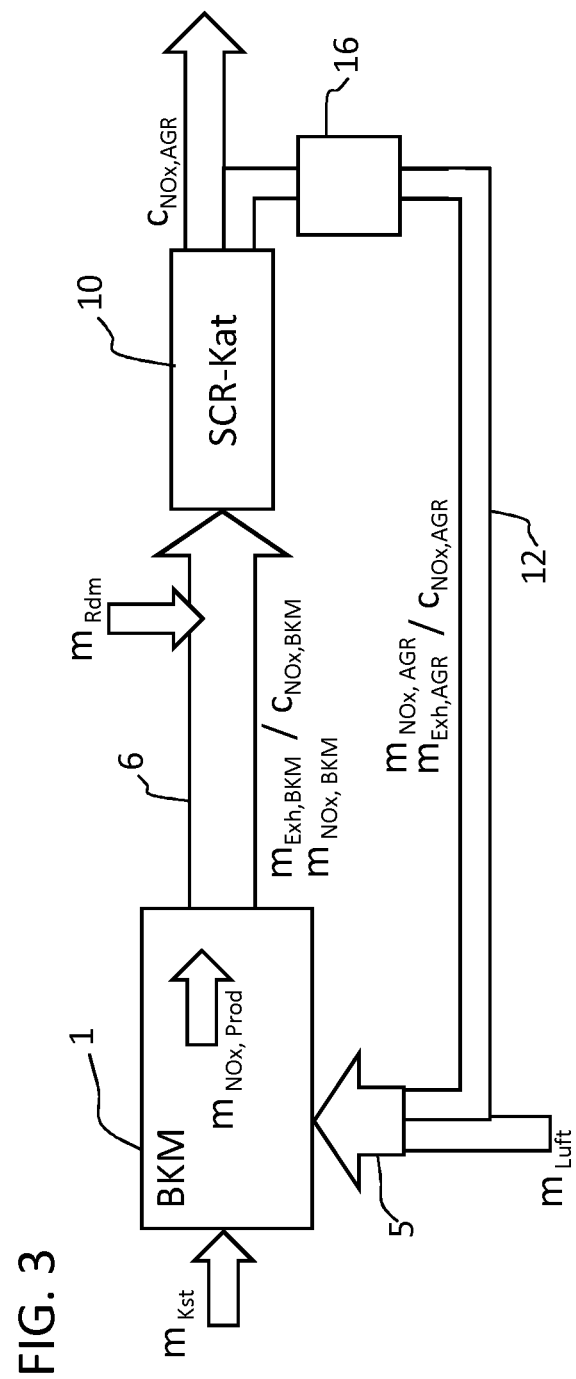
FIG. 3 is a drawing showing an illustration of the mass flows relevant to the method with regard to the internal combustion engine and the SCR catalytic converter.

The determination of the efficiency of the SCR catalytic converter 10 is based on the following fundamental physical-mathematical relationships, for the understanding of which consideration may be given to FIG. 3:

$$m_{Exh,BKM} = m_{Kst} + m_{Luft} + m_{Exh,AGR}$$

Here, $m_{Exh,BKM}$ is the exhaust-gas mass flow output from the internal combustion engine 1 into the exhaust-gas duct 6, $m_{Luft}$ is the fresh air mass flow supplied to the internal combustion engine 1 via the intake region 5, $m_{Kst}$ is the fuel mass flow supplied to the internal combustion engine for combustion, and $m_{Exh,AGR}$ is the partial mass flow of the exhaust gas recirculated via the low-pressure exhaust-gas recirculation line 12 and the intake region 5 to the internal combustion engine 1. For the mass flow of the nitrogen oxide $m_{NOx,BKM}$ output from the internal combustion engine 1, the following applies accordingly:

$$m_{NOx,BKM} = m_{NOx,AGR} + m_{NOx,Prod}$$

Here, $m_{NOx,AGR}$ is the mass flow of the nitrogen oxide recirculated via the low-pressure exhaust-gas recirculation line 12 and $m_{NOx,Prod}$ is the nitrogen oxide mass flow produced by the internal combustion engine 1 during the combustion process. For the nitrogen oxide mass flow contained in the exhaust-gas mass flow, the following relationship also applies:

$$m_{NOx} = c_{NOx} * M_{NOx} / M_{Exh} * m_{Exh}$$

Here, $m_{NOx}$ is the mass flow fraction of the nitrogen oxides contained in the total exhaust-gas mass flow $m_{Exh}$, $c_{NOx}$ is the volume concentration of the nitrogen oxides, $M_{NOx}$ is the mean molar mass of the nitrogen oxides, and $M_{Exh}$ is the mean molar mass of the total exhaust-gas mass flow. This relationship can be applied correspondingly to the mass flows $m_{NOx,BKM}$ and $m_{NOx,AGR}$ of the exhaust gas.

In an at least quasi-steady-state operating state of the internal combustion engine and thus of the device, it can also be assumed with good approximation that the nitrogen oxide mass flow $m_{NOx,Prod}$ produced by the internal combustion engine 1 during the combustion process is constant. Furthermore, for the nitrogen oxide mass flow produced, the following relationship applies:

$$m_{NOx,Prod} = (c_{NOx,BKM} * m_{Exh,BKM} - c_{NOx,AGR} * m_{Exh,AGR}) * M_{NOx}/M_{Exh}$$

In the abovementioned relationship, in the case of operating conditions being kept constant, only the values of the nitrogen oxide concentrations that can be correspondingly used in this relationship change when different reducing agent quantities or reducing agent mass flows $m_{Rdm}$ are added. For the efficiency $\eta_{SCR}$ of the SCR catalytic converter 10, the following relationship applies:

$$\eta_{SCR} = 1 - (c_{NOx,AGR} / c_{NOx,BKM})$$

The abovementioned relationship also applies accordingly when different reducing agent quantities or reducing agent mass flows $m_{Rdm}$ are added. Under the following boundary condition:

$$\alpha = m_{Rdm}/m_{Rdm,max},$$

where $m_{Rdm}$ denotes the presently added reducing agent mass flow and $m_{Rdm,max}$ denotes the maximum reducing agent mass flow stoichiometrically required for the complete reduction, and under the proviso that, for substoichiometric reducing agent metering and an approximately saturated catalytic converter, in particular in the case of a ratio $\alpha$ selected such that inhomogeneities of the reducing agent preparation or of the reducing agent supply are negligible, for example in the case of $\alpha \leq 0.9$ or $\alpha \leq 0.6$ or $\alpha \leq 0.4$, the efficiency of a fully functional SCR catalytic converter 10 corresponds approximately to the ratio $\alpha$, and thus the following applies with sufficient approximation:

$$\eta_{SCR} = \alpha$$

Applying the above equations to the addition of two different reducing agent mass flows, denoted below by the abbreviations R1 and R2 in the respective index, and correspondingly combining the relationships taking into account the stated approximations, the following relationship is obtained:

$$m_{Exh,AGR} = \frac{(C_{NOx,BKM,R2} - C_{NOx,BKM,R1}) * (m_{Kst} + m_{Luft})}{C_{NOx,BKM} * \alpha_{R1} - C_{NOx,BKM,R2} * \eta_{SCR,R2}}$$

From the abovementioned equation, the efficiency of the SCR catalytic converter 10, for example for the reducing agent mass flow indicated by R2, can be ascertained by conversion as follows:

$$\eta_{SCR,R2} = \frac{C_{NOx,BKM,R1}}{C_{NOx,BKM,R2}} * \alpha_{R1} - \frac{C_{NOx,BKM,R1} - C_{NOx,BKM,R2}}{C_{NOx,BKM,R2}} * \frac{m_{Kst} + m_{Luft}}{m_{Exh,AGR}}$$

The physical-mathematical relationship presented here for determining the efficiency of the SCR catalytic converter includes substantially the nitrogen oxide concentrations measurable by means of the nitrogen oxide sensor in the presence of a first predefined reducing agent mass flow, $c_{NOx,BKM,\ R1}$, and of a further reducing agent mass flow, $c_{NOx,BKM,R2}$, and also the mass flows, known from the control of the internal combustion engine, of the supplied fuel $m_{Kst}$ and of the supplied air $m_{Luft}$ and furthermore of the partial mass flow, predefined in the method, of the exhaust gas $m_{Exh,AGR}$ recirculated via the low-pressure exhaust-gas recirculation line 12 and the intake region 5 to the internal combustion engine 1. Thus, all required variables for the determination of the efficiency of the SCR catalytic converter are known.

The physical-mathematical relationship presented here may for example be stored as a computational algorithm in the electronic memory unit connected to the electronic control unit and can be executed by the electronic control unit for the purposes of determining the efficiency.

What is claimed is:

1. A method for determining the efficiency of an SCR catalytic converter of an exhaust-gas aftertreatment device of an internal combustion engine, wherein the SCR catalytic converter is disposed downstream of the internal combustion engine in an exhaust-gas duct with regard to the exhaust-gas mass flow, a nitrogen oxide sensor and a metering device for adding a reducing agent are both arranged in the exhaust-gas duct between the internal combustion engine and the SCR catalytic converter, and a low-pressure exhaust-gas recirculation line with an exhaust-gas recirculation valve is disposed between the exhaust-gas duct downstream of the SCR catalytic converter and an intake region of the internal combustion engine, the method comprising:
    setting or identifying quasi-steady-state operating state of the internal combustion engine and an associated exhaust-gas recirculation rate in the low-pressure exhaust-gas recirculation line;
    adding a first predefined reducing agent quantity using the metering device into the exhaust-gas duct;
    measuring a resulting first nitrogen oxide value using the nitrogen oxide sensor;
    adding a further predefined reducing agent quantity, different from the first reducing agent quantity, using the metering device;
    measuring the resulting further nitrogen oxide values using the nitrogen oxide sensor; and
    determining the efficiency of the SCR catalytic converter based at least in part on the associated exhaust-gas recirculation rate and the measured nitrogen oxide values.

2. The method as claimed in claim 1, wherein there is an oxidation catalytic converter arranged in the exhaust gas duct between the internal combustion engine and the metering device.

3. The method as claimed in claim 1, wherein, in the course of the at least quasi-steady-state operating state, operating parameters of the internal combustion engine are selected such that an exhaust-gas temperature that is elevated in relation to normal operation results therefrom, whereby the nitrogen oxide storage capacity of the SCR catalytic converter is minimized.

4. The method as claimed in claim 1, wherein the first quantity and/or the further quantity are smaller than a maximum reducing agent quantity required for complete reduction of the nitrogen oxides in the exhaust-gas mass flow.

5. The method as claimed in claim 4, wherein the first quantity and/or the further quantity are such that the ratio α of the added reducing agent quantity to the maximum reducing agent quantity is less than or equal to 0.9.

6. The method as claimed in claim 5, wherein the ratio of the further added reducing agent quantity to the maximum reducing agent quantity differs from the ratio of the previously added reducing agent quantity to the maximum reducing agent quantity by an amount greater than or equal to 0.3.

7. A device for determining the efficiency of an SCR catalytic converter of an exhaust-gas aftertreatment device of an internal combustion engine having an exhaust-gas duct in which the SCR catalytic converter is arranged downstream of the internal combustion engine with regard to the exhaust-gas mass flow, a nitrogen oxide sensor and a metering device for adding a reducing agent arranged in the exhaust-gas duct upstream of the SCR catalytic converter, and a low-pressure exhaust-gas recirculation line with an exhaust-gas recirculation valve from the exhaust-gas duct downstream of the SCR catalytic converter to an intake region of the internal combustion, the device has comprising:
    an electronic control unit programmed to:
    set or identify a quasi-steady-state operating state of the internal combustion engine and an associated exhaust-gas recirculation rate in the low-pressure exhaust-gas recirculation line;
    trigger the metering device to add a first predefined reducing agent quantity into the exhaust-gas duct;
    trigger the nitrogen oxide sensor to measure a resulting first nitrogen oxide value;
    trigger the metering device to add a further predefined reducing agent quantity, different from the first reducing agent quantity;
    trigger the nitrogen oxide sensor to measure the resulting further nitrogen oxide values; and
    calculate the efficiency of the SCR catalytic converter based at least in part on the associated exhaust-gas recirculation rate and the measured nitrogen oxide values.

8. The device as claimed in claim 7, wherein there is an oxidation catalytic converter arranged in the exhaust gas duct between the internal combustion engine and the metering device.

9. The device as claimed in claim 7, wherein the electronic control unit includes an electronic memory unit storing data including information and algorithms for determining the efficiency of the SCR catalytic converter.

10. The device as claimed in claim 9, wherein the electronic memory unit stores data including at least one datum selected from the group consisting of
    setting or identifying an at least quasi-steady-state operating state of the internal combustion engine,
    specifying the exhaust-gas recirculation rate in the low-pressure exhaust-gas recirculation line by means of the exhaust-gas recirculation valve and/or regarding the air mass flow to be supplied to the internal combustion engine and/or, and regarding the fuel mass flow to be supplied to the internal combustion engine.

* * * * *